US00PP31597P2

(12) United States Plant Patent
Snijder

(10) Patent No.: US PP31,597 P2
(45) Date of Patent: Mar. 24, 2020

(54) ***PELARGONIUM* PLANT NAMED 'PEQZ0064'**

(50) Latin Name: *Pelargonium interspecific*
Varietal Denomination: PEQZ0064

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,876

(22) Filed: Jan. 28, 2019

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./263.1, 324, 325, 330
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Pelargonium* plant named 'PEQZ0064' particularly distinguished by the bright red colored inflorescences held above the dark green foliage, heat and drought tolerant on a semi-trailing plant habit.

1 Drawing Sheet

Latin name of the genus and species of the plant claimed: *Pelargonium interspecific.*

Varietal denomination: 'PEQZ0064'.

BACKGROUND OF THE NEW PLANT

The present invention comprises a new *Pelargonium*, botanically known as *Pelargonium interspecific*, and hereinafter referred to by the variety name 'PEQZ0064'.

'PEQZ0064' is a product of a planned breeding program. The new cultivar 'PEQZ0064' has bright red colored intlorescences held above the dark green foliage, heat and drought tolerant on a semi-trailing plant habit.

'PEQZ0064' originates from a hybridization in a controlled breeding program made in February 2011, in a greenhouse in Amatitlán, Guatemala. The female parent was an unpatented, proprietary plant of *P. interspecific* parentage, identified as 'k04-9123-2' with single scarlet red colored florets when compared to 'PEQZ0064'.

The male parent of 'PEQZ0064' was an unpatented, proprietary plant of *P. peltatum* parentage, identified as 'PEL-095067-02' with more pink colored florets and a more open plant habit when compared to 'PEQZ0064'. The resultant seed was sown in December 2011.

'PEQZ0064' was selected as one flowering plant within the progeny of the stated cross in April 2012 in a greenhouse in Enkhuizen, The Netherlands.

The first act of asexual reproduction of 'PEQZ0064' was accomplished when vegetative cuttings were propagated from the initial selection in the May 2012 in a greenhouse in Enkhuizen, The Netherlands.

BRIEF SUMMARY OF INVENTION

Horticultural examination of plants grown from cuttings of the plant initiated in June 2012 in Enkhuizen, the Netherlands, and continuing thereafter, has demonstrated that the combination of characteristics as herein disclosed for 'PEQZ0064' are firmly fixed and are retained through successive generations of asexual reproduction.

'PEQZ0064' has not been observed under all possible environmental conditions. The phenotype may vary significantly with variations in environment such as temperature, light intensity, and day length.

A Plant Breeder's Right for this cultivar has not yet been applied for. 'PEQZ0064' has not been made publicly available prior to the effective filing date of this application, notwithstanding any disclosure that may have been made less than one year prior to the effective filing date of this application by the inventor or another who obtained 'PEQZ0064' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0064' with colors being as true as possible with an illustration of this type.

Figure 1:
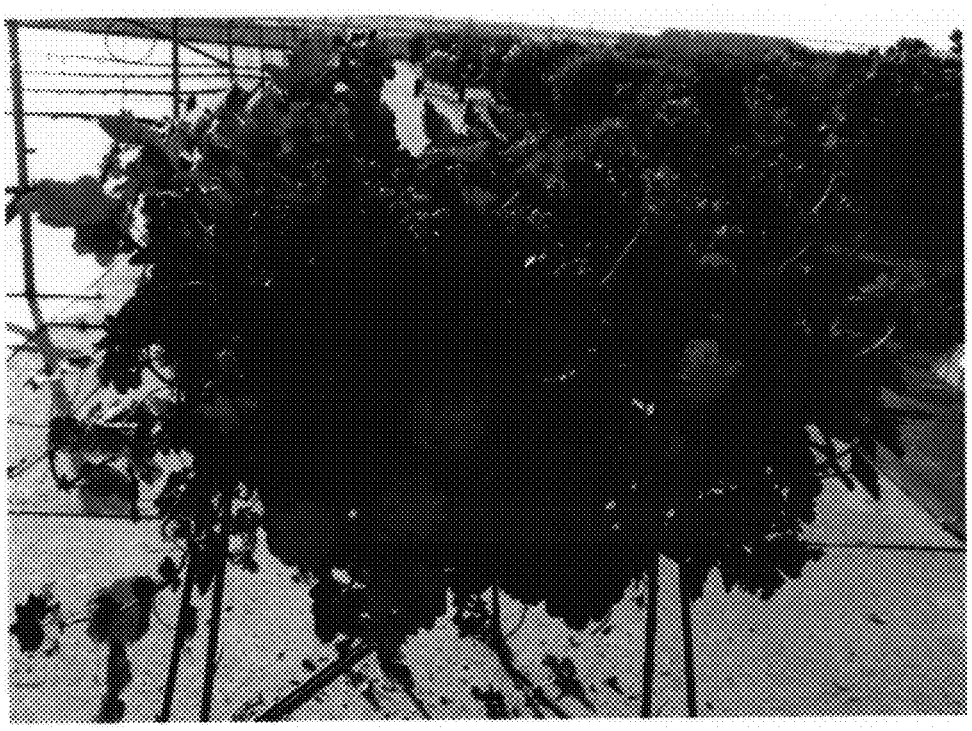
Figure 2:
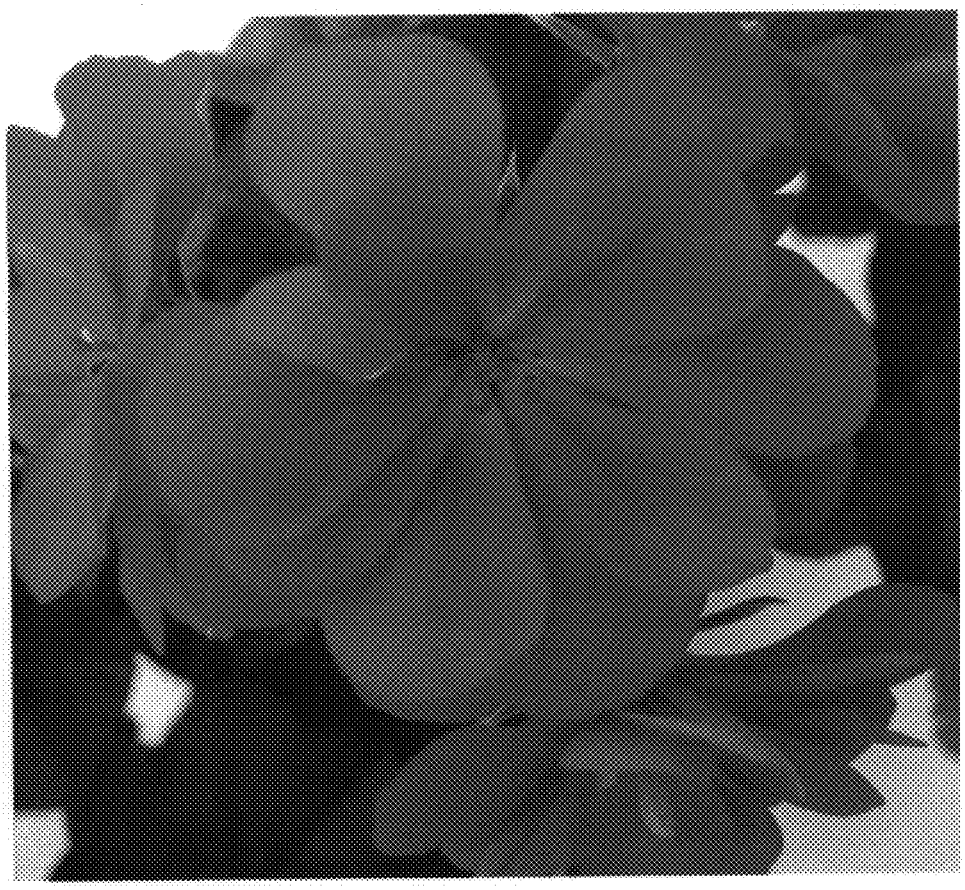

The photographic drawings in FIG. 1 shows a basket with 4 flowering plants of the new variety and FIG. 2, a close-up of the flower.

DETAILED BOTANICAL DESCRIPTION

The plant descriptions and measurements were taken in Andijk, The Netherlands in September under natural light. These plants were approximately 12 weeks old and were grown in a 1 gallon pots, in a greenhouse trial. The plants shown in the photographs were about 26 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PEQZ0064' AND A MOST SIMILAR VARIETY

| | 'PEQZ0064' | 'Fismaxi' (U.S. Plant Pat. No. 16,683) |
|---|---|---|
| Foliage color: | Dark green | Green |
| Corolla color: | Red towards burgundy | Red towards orange |

Plant:
- *Form, growth and habit.*—Spreading to semi-trailing.
- *Plant height.*—14-18 cm.
- *Plant height (inflorescence included).*—18-22 cm.
- *Plant width.*—45-50 cm per plant.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Immature leaf, color upper surface.*—Closest to RHS 137A.
- *Immature leaf, lower surface.*—Between RHS 137C and RHS 146A.
- *Mature leaf, color upper surface.*—Closest to RHS 137A.
- *Mature leaf, lower surface.*—Between RHS 137C and RHS 146A.
- *Length.*—About 4.0-4.5 cm.
- *Width.*—About 6.0-9.0 cm.
- *Shape.*—Orbicular.
- *Base shape.*—Cordate, heart-shaped.
- *Apex shape.*—Rounded, waved but with a rather sharp tip.
- *Margin.*—Wavy, undulate margins with rather sharp tips.
- *Texture upper side.*—Pilose.
- *Texture lower side.*—Pilose.
- *Leaf zonation color.*—RHS 202A.
- *Color of veins, upper surface.*—Closest to RHS 144A, becoming indistinct.
- *Color of veins, lower surface.*—Closest to RHS 144A, becoming indistinct.
- *Pattern of veining.*—Palmate.
- *Petiole color.*—Closet to RHS 144A.
- *Petiole length.*—Range: 2.0-9.0 cm.
- *Diameter of petiole.*—0.2-0.3 cm.
- *Texture.*—Pilose hairs.

Stem:
- *Quantity of branches.*—5-7 branches extending from base, lateral branches not included in counting.
- *Color of stem/branches.*—Parts of stem/branches with strong anthocyanins. Green/younger parts: closest to RHS 144A and RHS 144B.
- *Length of stem/branches.*—30-60 cm.
- *Diameter.*—0.5-0.6 cm.
- *Length of internodes.*—Range: 2.0-7.0 cm.
- *Texture.*—Hirsute, pilose hairs.

Peduncle:
- *Color of peduncle.*—Closest to RHS 144A with anthocyanins of color closest to RHS 187A.
- *Length of peduncle.*—8.0-18.0 cm.
- *Peduncle diameter.*—0.3-0.4 cm.
- *Texture.*—Hirsute.

Pedicel:
- *Color of pedicel.*—Closest to RHS 187A and RHS 187B.
- *Length of pedicel.*—2.0-2.2 cm.
- *Diameter of pedicel.*—0.15-0.2 cm.
- *Texture.*—Pilose.

Bud (just before opening):
- *Color.*—Closest to RHS 45B but whiter.
- *Length.*—1.5 cm.
- *Width.*—0.7-0.8 cm.
- *Shape.*—Elliptical.

Inflorescence:
- *Type.*—Umbel, semi-spherical.
- *Lastingness of individual flowers.*—7-9 days at 18° C. temperature.
- *Number of inflorescences per plant.*—15 mature and 20-25 immature umbels in various stages.
- *Fragrance.*—None.
- *Umbel diameter.*—About 5.0-8.0 cm.
- *Umbel depth.*—4.5-5.0 cm.

Corolla:
- *Form.*—Semi-double.
- *Number of petals.*—10-14.
- *Diameter of flower.*—About 4.5 cm.
- *Depth of flower.*—1-1.5 cm.
- *Color upper petals, upper surface.*—Burgundy red with an almost velvet appearance, closest to RHS 45B but a more vibrant and deeper red.
- *Color upper petals, lower surface.*—Closest to RHS 45B but much whiter.
- *Length of upper petals.*—2.3-2.5 cm.
- *Width of upper petals.*—1.0-1.2 cm.
- *Color lower petals, upper surface.*—Burgundy red with an almost velvet appearance, closest to RHS 45B but a more vibrant and slightly darker red; Deep dark-red marking (stripes) at the base.
- *Color lower petals, lower surface.*—Closest to RHS 45B but much whiter.
- *Length of lower petals.*—1.9-2.1 cm.
- *Width of lower petals.*—1.1-1.3 cm.
- *Petal shape.*—Obovate to spatulate.
- *Apex shape.*—Rounded.
- *Margin.*—Entire.
- *Base.*—Attenuate.
- *Petal texture.*—Pilose on both surfaces.

Calyx:
- *Number of sepals.*—5.
- *Color of sepals.*—Closest to RHS 144A and RHS 144B, covered with anthocyanins closest to RHS 187B and RHS 187C.
- *Length of sepals.*—1.3-1.5 cm.
- *Width of sepals.*—0.3-0.4 cm.
- *Sepal shape.*—Lanceolate to enciform.
- *Apex shape.*—Acute, but with a sharp tip.
- *Margins.*—Entire.
- *Texture, upper surface.*—Pilose.
- *Lower surface.*—Pilose.

Reproductive organs:

Gynoecium:
- *Pistil.*—1.
- *Length.*—1-1.1 cm.
- *Style color.*—Base: closest to RHS 145D; apex: closest to RHS 187A and RHS 187B.
- *Style length.*—0.5-0.6 cm.
- *Stigma color.*—Closest to RHS 187A and RHS 187B.

*Ovary color*.—Closest to RHS 145A.
*Ovary length*.—0.4-0.5 cm.
*Ovary diameter*.—About 0.3 cm.

Androecium:

*Number of stamens*.—7-9.
*Color of filaments*.—Apex closest to RHS 45B but whiter, base closest to RHS 155C.
*Length filaments*.—1.0-1.2 cm.
*Anther color*.—Closest to RHS 71A.
*Length of anthers*.—About 0.3 cm.
*Color of pollen*.—No pollen detected.
*Pollen amount*.—None.
*Fertility/seed set*.—Has not been determined to date.
*Disease/pest resistance*.—Has not been determined to date.

What is claimed is:

1. A new and distinct variety of *Pelargonium* plant named 'PEQZ0064' substantially as illustrated and described herein.

* * * * *